(12) United States Patent
Kustu et al.

(10) Patent No.: US 6,242,189 B1
(45) Date of Patent: Jun. 5, 2001

(54) SELECTIVE ISOLATION OF BACTERIAL MRNA

(75) Inventors: Sydney G. Kustu, Berkeley, CA (US); Volker F. Wendisch, Juelich (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/410,855

(22) Filed: Oct. 1, 1999

(51) Int. Cl.[7] ............................ C12Q 1/68; C12Q 1/48; C12N 9/12; C12N 1/20; C12N 15/09; C07H 21/00; C07H 21/02
(52) U.S. Cl. ............................ 435/6; 435/15; 435/259; 435/194; 435/69.2; 435/243; 435/252.33; 536/25.4
(58) Field of Search ..................... 435/6, 69.2, 194, 435/252.3, 320.1, 243, 287.2, 68.1, 7.3, 737, 252.33, 822, 849, 15, 259; 536/23.1, 25.4

(56) References Cited

U.S. PATENT DOCUMENTS 5,525,497 * 6/1996 Keller et al. ........................ 435/194
5,968,767 * 10/1999 Sheikh et al. ....................... 435/68.1
5,972,693 * 10/1999 Rothberg et al. .................. 435/287.2
5,997,913 * 12/1999 Fowler et al. ......................... 426/15

OTHER PUBLICATIONS

Amara et al. Specific polyadenylation and purification of total messenger RNA from *Escherichia coli*. Nucleic acids Reserch. vol. 25, No. 17, pp. 3465–3470, Dec. 1997.

* cited by examiner

Primary Examiner—Stephanie W. Zitomer
Assistant Examiner—Cynthia B. Wilder
(74) Attorney, Agent, or Firm—Richard Aron Osman

(57) ABSTRACT

The invention provides methods and compositions for selectively isolating total bacterial mRNA. The general method comprises contacting a bacterial lysate comprising total bacterial mRNA and nonisolated bacterial polysomes with an exogenous enzyme under conditions wherein the enzyme selectively modifies the mRNA to form modified mRNA, and isolating the modified mRNA. In particular embodiments, the enzyme is selected from a poly(A) polymerase, a RNA ligase and a terminal deoxynucleotidyl transferase. Depending on the enzyme, the modified mRNA may have any of a variety of modifications, such as a 3' tail, particularly a poly(A) tail, a specific sequence tag, a detectably labeled nucleotide, etc.

13 Claims, No Drawings

SELECTIVE ISOLATION OF BACTERIAL MRNA

INTRODUCTION

1. Field of the Invention

The field of the invention is the selective isolation of bacterial mRNA.

2. Background of the Invention

RNA exists in three functionally different forms: ribosomal RNA (rRNA), transfer RNA (tRNA) and messenger RNA (mRNA). Whereas stable rRNA and tRNA are involved in catalytic processes in translation, mRNA molecules carry genetic information. Only about 1–5% of the total RNA consists of mRNA, about 15% of tRNA and about 80% of rRNA. In eukaryotic cells mRNA is polyadenylated (the 3'-terminal modification usually consists of about 200 adenosyl residues) and differs from rRNA and tRNA by this structural feature (Hereford & Roshbash (1977) Cell 10:453–462). Thus, eukaryotic mRNA can easily be purified by chromatography based on hybridization to oligo(dT)-nucleotides.

Bacterial mRNA, however, is not uniformly polyadenylated and only a few mRNA molecules have short 3'-terminal modifications (Nakazato et al. (1975) Nature 256:144–146; Sarkar (1997) Ann. Rev. Biochem. 66:173–197). Thus, in bacteria mRNA cannot be distinguished from rRNA or tRNA by a structural feature.

In the bacterial cell, rRNA is complexed with ribosomal proteins to high molecular weight structures: sub-ribosomal 30S and 50S particles, 70S ribosomes and polysomes. Polysomes represent a complex of an mRNA molecule with one or more ribosomes bound to it and polysomes can be purified. Amara & Vijaya showed that when purified polysomes are subjected to polyadenylation in vitro only the 3'-termini of mRNA, but not of rRNA are modified (Amara & Vijaya (1997) Nucl. Acid Res. 25:3465–3470). Their finding suggested that 3'-termini of rRNA in complexes with ribosomal proteins (at least in polysomes) are sterically blocked. However, mRNA molecules present in polysomes are only a subset of all cellular mRNA as those mRNA molecules are actively transcribed. To avoid biasing mRNA purification for actively transcribed mRNA molecules, we developed a method that allows isolation of mRNA representing all of the cellular mRNA population.

SUMMARY OF THE INVENTION

The invention provides methods and compositions for selectively isolating total bacterial mRNA. The general method comprises the steps of (a) contacting a bacterial lysate comprising total bacterial mRNA and nonisolated bacterial polysomes with an exogenous enzyme under conditions wherein the enzyme selectively modifies the mRNA to form modified mRNA, and (b) isolating the modified mRNA. In particular embodiments, the enzyme is selected from a poly(A) polymerase, a RNA ligase and a terminal deoxynucleotidyl transferase. Depending on the enzyme, the modified mRNA may have any of a variety of modifications, such as a 3' tail, particularly a poly(A) tail, a specific sequence tag, a detectably labeled nucleotide, etc.

The conditions generally comprise an inhibitor of RNases, such as one or more chemical inhibitors and/or elevated temperature, used especially in conjunction with a thermostable enzyme. The subject compositions include products of the disclosed methods, particularly compositions comprising total bacterial mRNA, including species not of or from intact polysomes, wherein the mRNA is 3' polyadenylated.

DETAILED DESCRIPTION OF SPECIFIC EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or, polynucleotide sequences are understood to encompass opposite strands.

The general method involves contacting a bacterial lysate comprising total bacterial mRNA and nonisolated bacterial polysomes with an exogenous enzyme under conditions wherein the enzyme selectively modifies the mRNA to form modified mRNA and then isolating the modified mRNA.

The method is generally applicable to a wide variety of bacteria and lysates. For example, total mRNA is shown to be selectively isolated from lysates of bacterial species from diverse phyla and classes, including those of Aquifecales, Thermotogales, Thermodesulfobacterium, Thermus-Deinococcus group, Chloroflecales, Cyanobacteria, Firmicutes, Leptospirillum group, Synergistes, Chlorobium-Flavobacteria group, Chlamydia-Verrucomicrobia group, Planctomycetales, Flexistipes, Fibrobacter group, spirochetes, Proteobacteria and Archaebacteria. Preferred bacteria of particular laboratory and/or commercial significance are listed in Tables 1A and 1B.

TABLE 1A

Method-suitable gram negative bacteria.

| 1. Spirochetes | 6. Salmonella | 11. Pastueurella |
|---|---|---|
| 2. Spirillum | 7. Shigella | 12. Haemophilus |
| 3. Campylobacter | 8. Proteus | 13. Bacteroides |
| 4. Klebsiella | 9. Neisseria | 14. Rhizobium |
| 5. Vibrio | 10. Rickettsia | 15. Chlamydia |

TABLE 1B

Method-suitable gram positive bacteria.

| 1. Staphylococcus | 6. Bacillus licheniformis | 11. Propionobacter |
|---|---|---|
| 2. Streptococcaceae | 7. Bacillus thuringiensis | 12. Pseudomfilamentous Rods |
| 3. Lactobacillus | 8. Enterobacter | 13. Streptomyces |
| 4. Clostridium | 9. Listeria | 14. Mycoplasma |
| 5. Bacillus subtilis | 10. Arthrobacter | 15. Mycobacteria |

A wide variety of starting materials and lysates may be used. For example, lysates may be produced by mechanical compression or agitation, osmotic shock, sonication, membrane permeablizers such as detergents and/or enzymes, etc. Essentially any starting material comprising the bacteria or lysate may be used; these include natural or laboratory grown colonies and material infected or otherwise colonized by the bacteria. In a particular embodiment, the starting material comprises a bacterially infected eukaryotic organism, tissue or extract or fraction thereof, e.g. Rhizobium infected plant material.

The lysates comprise total mRNA, meaning a relatively unbiased (as compared with intact polysomal mRNA) representation of all bacterial mRNA irrespective of whether actively transcribed or incorporated in intact polysomes. Total mRNA is distinguishable from selected mRNA subsets which exclude or limit certain types of mRNA, e.g. by imposing size or function limitations. For example, intact polysomal mRNA fractions exclude mRNA species not complexed with intact polysomes, whereas total mRNA, as used herein, necessarily includes bacterial mRNA species beyond those of intact polysomes.

The targeted total bacterial mRNA is contacted with exogenous enzyme (i.e. beyond what is already present in the lysate) which selectively modifies the mRNA. In general, the modification provides convenient means for separating the modified mRNA from other RNA species, e.g. tRNA and rRNA, of the lysate. A wide variety of enzymes and resulting modifications may be used. In particular embodiments, the modification is a 5' or 3' tag, particularly a 3' tag, particularly a 3' oligonucleotide tag. Such tags may be introduced with a variety of enzymes such as RNA ligases, RNA polymerases (e.g. Taq, Klenow, T7 RNA polymerase, HIV reverse transcriptase, 3D$^{pol}$ RNA-dependent RNA polymerase, and polyA polymerase), terminal deoxynucleotidyltransferases, etc. These enzymes may be derived from a wide variety of prokaryotic and eukaryotic sources, many of which are commercially available and well-characterized.

By using particular nucleotides or nucleotide analogs, a wide variety of tags may be incorporated into the targeted mRNA. For example, rNTPs and/or dNTPs may be labeled with biotin, digoxigenin or fluorescein to create detectably and/or conveniently isolatable tags. In another embodiment, single nucleotide tag addition is effected with ddNTPs, cordycepin-5'-triphosphate (3'-dATP), etc.

The reaction or incubation conditions which permit the enzyme to modify the mRNA are readily determined empirically. In crude cell extracts obtained by a mechanical lysis procedure, rRNA should be in complexes with ribosomal proteins (30S, 50S, 70S ribosomes and polysomes) and their 3'-termini should be sterically blocked. tRNA is present, however, it occurs predominantly as amino-acylated form, and amino-acylation or 'charging' of tRNA occurs at the 3'-termini of tRNA, which thus is blocked. Uncharged tRNA bound to ribosomes elicits the stringent response (Lamod & Travers (1985) Cell 41:6–8). However, the 3'-termini of mRNA is accessible for polyadenylation regardless whether it is free or part of polysomal complexes.

The conditions generally include an inhibitor of RNase activity. A wide variety of a chemical RNase inhibitors and inhibitor cocktails are known in the art. In a particular embodiment, the inhibitor comprises an elevated temperature at which RNase activity is reduced to method-compatible levels. This embodiment entails the use of a modifying enzyme selected for thermostability, which may be selected empirically or readily extracted or derived from thermophilic or hyperthermophilic microbial species such as *Thermus aquaticus* and *Thermococcus litoralis, Bacillus stearothermophilus*.

Isolation of total mRNA is readily confirmed empirically by gene expression profile comparisons with total RNA extracted by conventional methods, e.g. hot phenol, as described below. Detailed exemplification for total mRNA isolation from *E. Coli* M G1655 lysates is described below and summary data of confirmed total mRNA isolations for several source materials and reaction conditions are shown in Table 2.

TABLE 2

Total mRNA isolations including source materials and reaction conditions.

| Starting Material | Enzyme | Modification | Reaction Conditions | Total mRNA Isolation |
|---|---|---|---|---|
| *E. coli* MG1655 mechanical lysate | *E. coli* Poly(A) polymerase | 3' poly A tag | 5 min at 37° C., 0.8 U/µl RNasin | + + + |
| *E. coli* MG1655 mechanical lysate | *S. cereviseae* Poly(A) polymerase | 3' poly A tag | 5 min at 30° C., 0.8 U/µl RNasin | + + + |
| *E. coli* MG1655 mechanical lysate | *T. aquaticus* Poly(A) polymerase | 3' poly A tag | 5 min at 58° C. | + + + |
| *E. coli* BL21(DE3) osmotic lysis | *E. coli* RNA ligase | 3' poly T tag | 5 min at 37° C., 0.8 U/µl RNasin | + + + |
| *E. coli* BL21(DE3) osmotic lysis | *S. cereviseae* RNA ligase | 3' poly G tag | 5 min at 30° C., 0.8 U/µl RNasin | + + + |
| *E. coli* BL21(DE3) osmotic lysis | *T. aquaticus* ligase | 3' poly CG tag | 5 min at 58° C. | + + + |
| *E. coli* MG1655 mechanical lysate | *E. coli* terminal deoxynucleotidyltransferases | 3' poly A tag | 5 min at 37° C., 0.8 U/µl RNasin | + + + |
| *Rhizobium* infected tobacco root stock, osmotic lysate* | *E. coli* Poly(A) polymerase | 3' poly A tag | 5 min at 37° C., 0.8 U/µl RNasin | + + + |
| *Neisseria* infected HeLa cells, osmotic lysate* | murine Poly(A) polymerase | 3' poly A tag | 5 min at 37° C., 0.8 U/µl RNasin | + + + |
| *Staphylococcus aureus* mechanical lysate | *E. coli* Poly(A) polymerase | 3' poly A tag | 5 min at 37° C., 0.8 U/µl RNasin | + + + |
| *Streptococcus pyogenes* mechanical lysate | *E. coli* Poly(A) polymerase | 3' poly A tag | 5 min at 37° C., 0.8 U/µl RNasin | + + + |
| *Bacillus cereus* mechanical lysate | *E. coli* Poly(A) polymerase | 3' poly A tag | 5 min at 37° C., 0.8 U/µl RNasin | + + + |

TABLE 2-continued

Total mRNA isolations including source materials and reaction conditions.

| Starting Material | Enzyme | Modification | Reaction Conditions | Total mRNA Isolation |
|---|---|---|---|---|
| E. coli MG1655 mechanical lysate | D. Melanogaster Poly(A) polymerase | 3' poly A tag | 5 min at 25° C., 0.8 U/µl RNasin | + + + |
| E. coli MG1655 mechanical lysate | C. elegans Poly(A) polymerase | 3' poly A tag | 5 min at 25° C., 0.8 U/µl RNasin | + + + |

*plant/cellular mRNA depleted by polyT adsorption

Polyadenylation and purification of a test mRNA. A radioactively labeled test mRNA molecule was synthesized in vitro using EcoRV-restricted plasmid pJES311 (containing S. typhimurium ntrC), T7-RNA-polymerase and α-$^{32}$P-ATP. The labeled test mRNA was added to crude extracts of E. coli MG1655 obtained by bead-beating with zirconium/glass beads in a buffer containing 400 µM ATP, 250 mM NaCl, 0.01 U/µl DNase 10 mM MgCl$_2$, 0.8 U/µl RNasin, 5 mM MnCl$_2$, 40 mM Tris, pH 8.0. This mixture was divided into two aliquots and to one of them purified 16 U/ml His-tagged E. coli poly(A) polymerase was added. E. coli poly(A) polymerase was expressed as N-terminally His- and FLAG-tagged protein in E. coli BL21(DE3) pLysE, Tn10, Dlac using plasmid pHF-PAP (Huang H., Liao J. and S. N. Cohen (1998) Nature 391:99–102). After nickel-chelate chromatography a poly(A) polymerase preparation was obtained that is essentially free of RNase contamination (after incubating 3.4 mg of the protein with 1 mg E. coli RNA for 30 minutes no degradation could be detected on agarose gels; data not shown). In the poly(A) polymerase preparation, 1 mg protein catalyzed the incorporation of 1.1 mmol of α-$^{32}$P-ATP per 10 min into acid-precipitable material (equivalent to 1100 U/mg).

The reaction without poly(A)polymerase and the reaction with 16 U/ml poly(A) polymerase both were incubated for 5 min at 37° C. After the incubation total RNA was prepared from these reactions and by oligo(dT)-chromatography fractions hybridizing to oligo(dT) were separated from those not binding to oligo(dT). Aliquots taken at different steps during the procedure were analyzed by denaturing polyacrylamide gel electrophoresis and subsequent densitometry. In the reaction without poly(A) polymerase, the test RNA exhibited unchanged gel mobility after 0.5 min and 2.5 min incubation and after preparation of total RNA from the reaction. When this RNA preparation was subjected to oligo(dT) chromatography more than 99% were found in the flow through and less than 1% bound to the oligo(dT) matrix. For the reaction with added poly(A) polymerase, gel mobility of the test RNA was changed to an apparent higher molecular weight already after 0.5 min of incubation. Total RNA from this reaction bound predominantly to the oligo (dT) matrix (>95%) and only a minor fraction was recovered in the flow through. This experiment indicates that a test RNA added to cell extracts can be polyadenylated and subsequently purified via oligo(dT) chromatography. Apparently, neither inhibitory compounds nor RNase activity which may be present in crude extracts abrogated polyadenylation in vitro.

Analysis of poly(A) tails generated by the in vitro protocol. For the analysis of poly(A) tails, crude cell extracts of E. coli were subjected to polyadenylation in the presence of α-$^{32}$P-ATP and RNA was purified by oligo(dT) chromatography as described above. The oligo(dT)-binding fraction should consist of cellular mRNA molecules with radiolabeled poly(A) tails. As analysed by denaturing polyacrylamide gel electrophoresis, the oligo(dT)-binding RNA showed a continuous size distribution without dominant signals corresponding to either rRNAs or tRNAs. Aliquots of the oligo(dT)-binding RNA were incubated with RNase T1 and RNase T2, respectively. After incubation with RNase T2, which shows no base specificity for hydrolysis, no radio-labeled RNA molecules could be detected. However, after incubation with RNase T1, which cleaves ribonucleic acids at guanidine residues and therefore leaves poly(A)-tails intact, RNA species ranging in size from about 20 to 120 nucleotides were detected. These results indicate that the poly(A) tails generated by in vitro polyadenylation of crude cell extracts are 20 to 120 nucleotides in length.

Determination of relative RNA levels before and after IPTG induction in total RNA and mRNA preparations. Isopropylthiogalactoside (IPTG) is the gratuitous inducer of the lactose operon (lacZYA operon). E. coli was cultivated on minimal medium with NH$_4$Cl and glycerol and 50 µM IPTG were added to exponentially growing cells. Before and 30 min after addition of IPTG aliquots were withdrawn. From these total RNA was prepared directly, mRNA was prepared via in vitro polyadenylation and specific β-galactosidase-activities were determined (lacZ codes for β-galactosidase). The specific β-galactosidase activity was increased about 75fold. Total RNA (10 µg each) and mRNA (0.3 µg each) were analysed by Northern dot blotting using probes specific for lacZ and as a control for dnaJ (RNA levels of dnaJ are expected not to change with varying IPTG concentrations). Hybridization with a probe complementary to lacZ RNA and densitometric analysis revealed a 30–35fold increase of lacZ RNA after IPTG Hybridization signals with the dnaJ probe indicated that dnaJ RNA levels did not change by IPTG addition. The signal intensities in the two hybridizations were similar for 10 µg total RNA and 0.3 µg mRNA indicating a 15–20fold enrichment of mRNA by the in vitro polyadenylation procedure. The nearly identical relative lacZ and dnaJ RNA ratios determined with total RNA preparations and mRNA preparations suggested that mRNA populations present in these two preparations are congruent.

Genome-wide expression analyses in E. coli on microarrays using total RNA and mRNA. Microarrays covering >95% of E. coli genes were prepared (described elsewhere). In order to determine whether genome-wide expression analyses on microarrays using total RNA and mRNA preparations yield congruent results, we again performed an IPTG induction experiment. IPTG is not metabolized by E. coli and specifically induces the transcription of the lacZYA operon. E. coli MG1655 was cultivated on C⁻N⁻ minimal medium with ammonium chloride and glycerol, 50 µM IPTG was added during the exponential growth phase. Before and 30 min after IPTG addition, total RNA was prepared by the hot-phenol method (Sambrook et al., 1989, Molecular Cloning: A laboratory manual, 2nd Ed., Cold Spring Harbor Laboratory Press, Cold Spring Harbor, N.Y.), mRNA was prepared by the selective in vitro polyadenylation procedure described herein and β-galactosidase was monitored according to Miller, 1972, Experiments in molecular genetics, p.352–355. Cold Spring Harbor Laboratory Press, Cold Spring Harbor, N.Y. The specific β-galactosidase (lacZ gene product) activity was increased 250-fold after IPTG induction.

Labeling of mRNA was similar as described by de Risi et al. (1997, Science 278:680–686) for S. cerevisiae and involved the reverse transcription of RNA into cDNA with fluorescent nucleotide analogs. However, both for E. coli total RNA and mRNA reverse transcription was primed by random oligonucleotides. Total RNA and mRNA isolated before IPTG addition were labeled using green-fluorescent Cy-3-dUTP, whereas total RNA and mRNA isolated 30 min after IPTG addition were labeled with red-fluorescent Cy-5-dUTP. cDNAs derived of total RNA before and after IPTG addition were mixed in a hybridization volume of 12 µl and hybridization to the E. coli microarray was performed at 65° C. for 5 hs. cDNAs derived of mRNA before and after IPTG addition were treated in the same way. Both the total RNA microarray and the mRNA microarray were washed stringetly and red- and green fluorescence were determined using an Axon confocal laser microscope scanner. The resulting red-green fluorescence images obtained for total RNA and for mRNA were subject to qualititive analysis. These hybridization data revealed, both for total RNA and for mRNA, increased relative RNA abundances for the lacZ, lacA and lacY genes after IPTG addition as hybridization signals are predominantly red-fluorescent.

Both experiments were analysed quantitatively in the following manner. For hybridization signals where both green and red fluorescence were at least five-fold above fluorescence background the ratio of net fluorescence intensities (i.e. after subtraction of background) reflected the relative RNA abundance. For hybridization signals where only one fluorescent intensity was at least five-fold above background a minimal relative RNA abundance was estimated from the ratio of absolute fluorescence intensities (i.e. without subtracting background signals). When both fluorescent signals are less than five-fold above background signals were considered too weak to be analysed quantitatively.

TABLE 3

Relative RNA abundances after IPTG addition relative to pre-IPTG addition

| gene | relative RNA abundance* | |
|------|------|------|
|  | mRNA | total RNA |
| lacZ | ≥32 | ≥34 |
| lacY | ≥24 | ≥66 |
| lacA | ≥22 | ≥24 |
| cynX | ≥4 | ≥8 |
| cirA | ≥5 | 8 |
| fepA | too weak | ≥4 |

*Only genes with at least four-fold relative RNA abundances are listed.

Relative RNA abundances in the IPTG experiment agreed for mRNA and total RNA also quantitatively (Table 3). For the reverse transcription reactions 20µg total RNA and 0.2 µmg mRNA, respectively, were used. This indicates that for the determination of relative RNA levels in genome-wide expression analyses a 100-fold reduced amount of mRNA is sufficient.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selectively isolating total bacterial mRNA comprising the steps of:

contacting a bacterial lysate comprising total bacterial mRNA and nonisolated bacterial polysomes with an exogenous enzyme under conditions wherein the enzyme adds a 3' tag to the total bacterial mRNA to form modified total bacterial mRNA, and isolating the modified total bacterial mRNA.

2. A method according to claim 1, wherein the enzyme is selected from a poly(A) polymerase, a RNA ligase and a terminal deoxynucleotidyl transferase.

3. A method according to claim 1, wherein the enzyme is an E. coli poly(A) polymerase.

4. A method according to claim 1, wherein the enzyme is thermostable.

5. A method according to claim 1, wherein the modified mRNA comprises a 3' oligonucleotide tail.

6. A method according to claim 1, wherein the modified mRNA comprises a 3' oligonucleotide tail comprising poly (A).

7. A method according to claim 1, wherein the modified mRNA comprises a detectable label.

8. A method according to claim 1, wherein the conditions include an inhibitor of RNases.

9. A method according to claim 1, wherein the conditions include an inhibitor of RNases selected from a chemical inhibitor cocktail and elevated temperature sufficient to inhibit the RNases.

10. A composition comprising total bacterial mRNA, including species not of or from intact polysomes, wherein the total bacterial mRNA is 3' polyadenylated.

11. A method according to claim 1, wherein the conditions include an inhibitor of RNases selected from a chemical inhibitor cocktail and elevated temperature sufficient to inhibit the RNases, wherein the elevated temperature is 58°C.

12. A method according to claim 1, wherein the enzyme is an E. coli poly(A) polymerase and the modified mRNA comprises a 3' oligonucleotide tail.

13. A method according to claim 1, wherein the enzyme is an E. coli poly(A) polymerase, the modified mRNA comprises a 3' oligonucleotide tail, and the conditions include an inhibitor of RNases.

* * * * *